United States Patent [19]

Ziegler et al.

[11] Patent Number: 5,135,748
[45] Date of Patent: Aug. 4, 1992

[54] COSMETIC COMPOSITION CONTAINING CATIONIC COMPONENTS

[75] Inventors: Philip D. Ziegler, Oxford; Michael C. Cheney, Fairfield, both of Conn.

[73] Assignee: Chesebrough-Pond's USA Co., Division of Conopco, Inc., Greenwich, Conn.

[21] Appl. No.: 662,680

[22] Filed: Feb. 28, 1991

[51] Int. Cl.$^5$ .............................. A61K 7/02
[52] U.S. Cl. .................... 424/401; 424/63; 514/777; 514/844; 514/845; 514/846; 514/847; 514/873; 514/937; 514/938; 514/975
[58] Field of Search ............. 424/63; 514/777–782, 514/772, 844–847, 873, 937, 938, 971, 975; 252/351

[56] References Cited

U.S. PATENT DOCUMENTS

| | | | |
|---|---|---|---|
| 4,209,449 | 6/1980 | Mayhew et al. | 260/403 |
| 4,389,418 | 6/1983 | Burton | 424/365 |
| 4,438,095 | 3/1984 | Grollier et al. | 424/70 |
| 4,503,002 | 3/1985 | Mayhew et al. | 260/945 |
| 4,663,159 | 5/1987 | Brode, II et al. | 424/70 |
| 4,772,689 | 9/1988 | Lang et al. | 514/844 X |
| 4,886,890 | 12/1989 | Chaudhuri et al. | 548/519 |

FOREIGN PATENT DOCUMENTS

| | | | |
|---|---|---|---|
| 2484419 | 3/1980 | France | 514/778 |
| 55-36412 | 12/1981 | Japan | 514/777 |

OTHER PUBLICATIONS

Monaquat P Series Technical Bulletin, Jul. 1981.
Quatrisoft Polymer LM-200 Technical Bulletin, 1987.
Crodata Bulletin, Jun. 1986.

*Primary Examiner*—Thurman K. Page
*Assistant Examiner*—James M. Spear
*Attorney, Agent, or Firm*—Milton L. Honig

[57] ABSTRACT

An aqueous composition is provided which includes from about 0.1 to about 30% by weight of a quaternary ammonium functionalized phosphate ester and from about 0.01 to about 10% by weight of a cationic polysaccharide. These compositions are freeze-thaw cycle stable and exhibit unusual skin mildness properties.

6 Claims, No Drawings

COSMETIC COMPOSITION CONTAINING CATIONIC COMPONENTS

BACKGROUND OF THE INVENTION

1. Field of the Invention

The invention relates to a cosmetic composition of improved physical stability and skin performance properties

2. The Related Art

Hosts of commercial emollient creams and lotions claim alleviation of the signs and symptoms of dry skin. Application of these products is intended to return skin to a normal condition by moisturizing and reducing evaporation of water from the skin. Most dry skin products are oil-in-water anionic or non-ionic emulsions. As a result, these products wash off with water and then must be re-applied.

Cationic emulsions occupy a much smaller market segment, but can possess certain skin feel advantages. In U.S. Pat. No. 4,389,418 (Burton) there is disclosed a water-out emulsion containing petrolatum or a mineral oil to moisturize the skin, a quaternary ammonium emulsifier, a fatty alcohol and a fatty ester emollient. Greaseless skin conditioning compositions based upon cationic polymers have also been reported in U.S. Pat. No. 4,438,095 (Grollier). Among the polymers disclosed are polyamines, polyaminoamides or quaternary polyammonium compounds. Emulsions are formed wherein the aqueous phase contains the cationic polymer and there are no detergent or foaming agents present.

Diquaternary nitrogen compounds have been reported in U.S. Pat. No. 4,886,890 (Chaudhuri et al) as useful in skin lotions and shampoos. These compositions may be formulated with a variety of detergents, such as sodium laureth-4 phosphate. Personal care products incorporating cationic polysaccharides have been described in U.S. Pat. No. 4,663,159 (Bróde et al). Emulsifiers in the form of phosphate quaternary compounds have been disclosed in U.S Pat. No. 4,209,449 and U.S. Pat. No. 4,503,002, each to Mayhew et al. These emulsifiers were said to be well tolerated by human tissue, exhibiting low irritation, and were stated to be suitable for use in cosmetics.

Skin moisture retention has been significantly increased by utilizing many of the cationic compounds mentioned in the above patents. Nonetheless, there remains considerable need for improvement for moisture retention. There are also the further problems of improving mildness and of providing stability against phase separation during freeze-thaw cycles.

Accordingly, it is an object of the present invention to provide a cosmetic composition of improved skin moisture retention.

Another object of the present invention is to provide a cosmetic composition having a relatively low human tissue irritancy.

A further object of the present invention is to provide a cosmetic composition in aqueous emulsion form whose phases resist separation even under extended freeze-thaw cycling.

These and other objects of the present invention will more readily become apparent from the description and examples which follow.

SUMMARY OF THE INVENTION

An aqueous composition is provided comprising:

(i) from about 0.10 to about 30% of a quaternary ammonium functionalized phosphate ester; and (ii) from about 0.10 to about 10% of a cationic polysaccharide.

The compositions of the present invention may either be oil-in-water or water-in-oil emulsions. Especially effective as the ester component are alkylamido quaternary ammonium phosphate esters. The cationic polysaccharide is especially effective when in the form of a cellulosic polymer quaternized with fatty alkyl groups.

DETAILED DESCRIPTION OF THE INVENTION

Now it has been discovered that a combination of a quaternary ammonium functionalized phosphate ester and a cationic polysaccharide can provide an aqueous composition with excellent freeze-thaw stability. Compositions of this invention demonstrate moisture retention after water washing which is significantly better than state-of-the-art products.

A quaternary ammonium functionalized phosphate ester is a necessary first component of the compositions of this invention. The phosphate ester will conform to the following general formula:

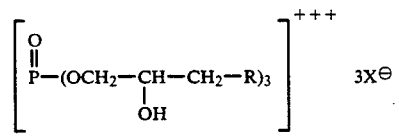

wherein R is a quaternary ammonium radical having from about 6 to about 40 carbons. This carbon atom limitation serves to include only materials of significant hydrophobic properties. The R radical can be cyclic or non-cyclic, aliphatic, aromatic or heterocyclic. X is an anion, such as halide, e.g., chloride.

In a preferred species, R is an amidoamine moiety of the formula:

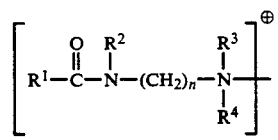

wherein $R^1$ is selected from the group consisting of alkyl, alkenyl, alkoxy and hydroxyalkyl having from 5 to 22 carbon atoms each, and from aryl and alkaryl having up to 20 carbon atoms;

$R^2$, $R^3$ and $R^4$ may each independently be selected from the group consisting of hydrogen, alkyl, hydroxyalkyl and alkenyl each having up to 6 carbon atoms, and from polyoxyalkylene of up to 10 carbon atoms;

$R^3$ and $R^4$ may additionally be selected from aceto and propriono groups and may even be taken together with the nitrogen to which they are attached so as to form a N-heterocyclic ring; and n is an integer from about 1 to 10.

In addition to the foregoing definitions where R is amidoamine, R may be a N-heterocyclic radical which may contain one additional hetero atom (e.g., oxygen or another nitrogen) and contains 5 to 6 total ring carbon atoms; optionally the heterocyclic radical may be substituted with alkyl and/or hydroxyalkyl of up to 20 carbon atoms each. Typical of such N-heterocyclic radicals are imidazolinyl, N-alkylmorpholino, alkylpyrimidino, alkyloxazolinyl, and the like. Such compounds may be represented by the formula:

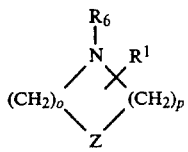

wherein

Z is N, S or O;

o is an integer from 0 to 3, p is an integer from 1 to 3, provided that the sum of o+p is from 3 to 4;

$R_1$ is a radical selected from the group consisting of alkyl, alkenyl, alkoxy and hydroxyalkyl units of from 2 to 22 carbon atoms each, and aryl and alkaryl of up to 20 carbon atoms; and $R^6$ is alkyl of from 2 to 6 carbon atoms which atoms may be substituted with a hydroxyl group.

Preferably R is derived from a tertiary amine radical of from about 10 to 40 carbon atoms. More preferred are tertiary amine radicals of the type ($C_6-C_{20}$ alkyl, dimethyl) amine such as N,N-dimethyl myristylamine, N,N-dimethyl-palmityl-amine, and N,N-dimethyllaurylamine.

Of most interest, are the phosphate esters identified as Formulas I through III. These are commercially available from Mona Industries, Inc., Paterson, New Jersey, sold under the Monaquat designation.

MONAQUAT P-TC, P-TD, P-TS, PHOSPHOLIPID EFA

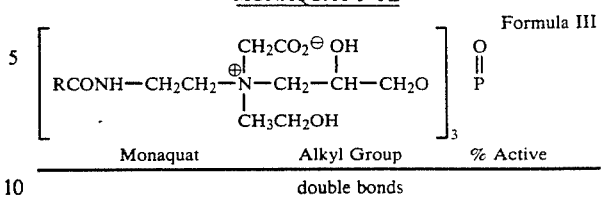

MONAQUAT P-TZ

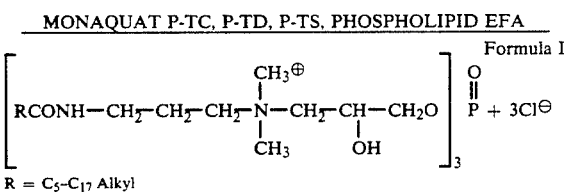

MONAQUAT P-TL

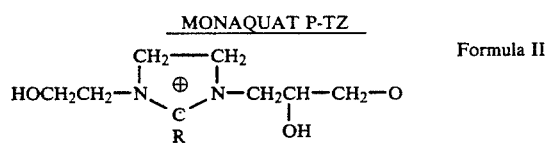

| Monaquat | Alkyl Group | % Active |
|---|---|---|
| P-TC | $C_5-C_{17}$ | 40.0 |
| P-TD | $C_{11}-C_{13}$ | 34.0 |
| P-TL | $C_{11}-C_{13}$ | 30.0 |
| P-TS | $C_{17}$ | 30.0 |
| P-TZ | $C_5-C_{17}$ | 30.0 |
| Phospholipid EFA | $C_{17}$ with 2 double bonds | 30.0 |

-continued

MONAQUAT P-TL

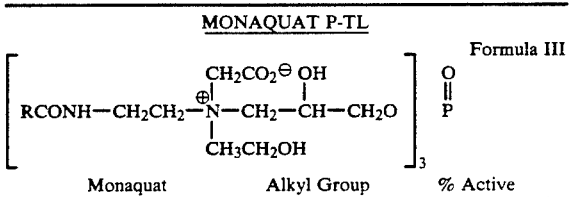

Most preferred from the above compounds are Monaquat P-TS, Monaquat P-TC, Monaquat P-TD and Phospholipid EFA.

Amounts of the quaternary phosphate ester will range from about 0.1 to about 30%, preferably from about 1 to about 15%, optimally between about 2 and 10% by weight of the composition.

A second essential component of the composition of this invention is a cationic polysaccharide. Polysaccharides of this invention are derived from naturally occurring polysaccharides or those modified by etherification, which are quaternized with a nitrogen-containing compound and alkylated with a compound, including a nitrogen-containing compound, containing a hydrophobe.

Polysaccharide starting materials include the naturally occurring, biosynthesized and derivatized carbohydrate polymers or mixtures thereof. Such materials encompass high molecular weight polymers composed of monosaccharide units joined by glycosidic bonds. These materials include the entire starch and cellulose families, pectin, chitosan; chitin; the seaweed products such as agar and carrageenan; alginate; the natural gums such as guar, arabic and tragacanth; bio-derived gums such as xanthan; and the like. Preferred starting materials include cellulosics conventionally employed for the preparation of cellulose ethers, such as chemical cotton, cotton linters, wood pulp, alkali cellulose, and the like and ether derivatives of the same. Such cellulose ethers include hydroxyethyl cellulose, hydroxypropyl cellulose, methyl cellulose, carboxymethyl cellulose, carboxyethyl cellulose, hydroxypropyl methyl cellulose, hydroxyethyl methyl cellulose, hydroxyethyl carboxymethyl cellulose, and the like. A particularly preferred polysaccharide starting material is hydroxyethyl cellulose. The polysaccharide starting material will possess a molecular weight corresponding to the number of polysaccharide repeat units, usually from 50 up to about 20,000. The molecular weight of the polysaccharides may be varied through controlled degradation procedures known in the art.

Etherified polysaccharides may be obtained commercially or produced from the polysaccharide starting materials mentioned previously. Etherification involves reacting pendent hydroxyl groups on the polysaccharide backbone with an etherifying agent, or mixtures thereof, which contain functional groups reactive with such hydroxyl groups. Etherification may be conducted to enhance the water-solubility of the polysaccharides, e.g. by ethoxylation. Typical etherifying agents include lower alkylating agents such as dimethyl sulfate, diethyl sulfate, methyl chloride, methyl bromide, ethyl chloride, ethyl bromide or n-propyl chloride; hydroxy alkylating agents such as ethylene oxide, propylene oxide or glycidol; and carboxy alkylating agents such as monochloroacetic acid, sodium chloroacetate or chloropropionic acid.

The polysaccharide starting materials are provided with quaternary nitrogen-containing substituents through quaternization reactions. Quaternization may be achieved by reacting the polysaccharides with quaternizing agents which are quaternary ammonium salts, including mixtures thereof, to effect substitution of the polysaccharide chain with quaternary nitrogen-containing groups. Typical quaternary ammonium salts which can be utilized include quaternary nitrogen-containing halides, halohydrins and epoxides. The quaternary ammonium salt may contain hydrophobes.

Particularly preferred are polymeric quaternary ammonium salts of hydroxyethyl cellulose reacted with a fatty alkyl dimethyl ammonium substituted epoxide. Illustrative preferred materials in this category are:

QUATRISOFT LM-200

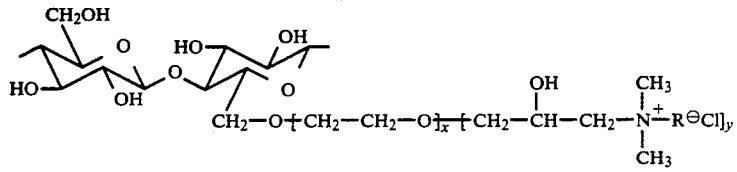

R = lauryl group

Formula IV

CRODACEL

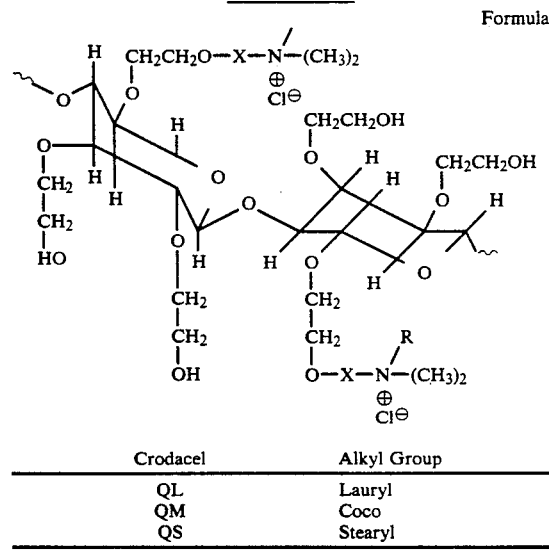

Formula V

| Crodacel | Alkyl Group |
|---|---|
| QL | Lauryl |
| QM | Coco |
| QS | Stearyl |

Preferred R groups will have a chain length ranging from about 10 to about 20 carbon atoms in length. These materials are available from the Union Carbide Corporation under the trademark Quatrisoft LM-200 and from Croda, Inc. under the trademark Crodacel Q (L, M and S).

Amounts of the cationic polysaccharide will normally range from about 0.01 to about 10%, preferably from about 0.01 to about 5%, optimally between about 0.2 and 1% by weight of the compositions.

Although the invention is not limited to cosmetic compositions in the form of emulsions, a particularly suitable vehicle is that of an emulsion. By definition, an emulsion is a dispersed system containing at least two immiscible liquid phases, one of which is dispersed in the form of small droplets throughout the other. Water and oil are the most common immiscible liquid phases. An emulsion in which oil is dispersed as droplets throughout the aqueous phase is termed an oil-in-water emulsion. When water is the dispersed phase and an oil is the dispersion medium, a water-in-oil emulsion exists. Contemplated within the scope of this invention are emulsions in the forms of lotions and creams of both types of emulsions, those where the water phase is continuous and those where the oil phase is continuous. The amounts of these phases may range from about 99:1 to 1:99 by weight.

Although the quaternary ammonium functionalized phosphate esters are intended as the primary emulsifier and surfactant for systems of this invention, there may also be present nonionic emulsifiers. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan, and hydrophilic wax esters. Amounts of the nonionic emulsifier may range anywhere from about 0.1 to about 20% by weight of the emulsion, preferably from about 2 to about 10% by weight.

A variety of oily emollients may be employed in the compositions of this invention. These emollients may be selected from one or more of the following classes:

1. Hydrocarbon oils and waxes. Examples thereof are mineral oil, petrolatum, paraffin, ceresin, ozokerite, microcrystalline wax, polyethylene, and perhydrosqualene.

2. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalane, and soybean oil.

3. Acetoglyceride esters, such as acetylated monoglycerides.

4. Ethoxylated glycerides, such as ethoxylated glyceryl monostearate.

5. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

6. Alkenyl esters of fatty acids having 10 to 20 carbon atoms. Examples thereof include oleyl myristate, oleyl stearate, and oleyl oleate.

7. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.

8. Fatty alcohols having 10 to 20 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.

19. Fatty alcohol ethers. Ethoxylated fatty alcohols of 10 to 20 carbon atoms including the lauryl, cetyl, stearyl, isostearyl, oleyl, and cholesterol alcohols, having attached thereto from 1 to 50 ethylene oxide groups or 1 to 50 propylene oxide groups.

10. Ether-esters such as fatty acid esters of ethoxylated fatty alcohols.

11. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

12. Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 mono- oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

13. Wax esters such as beeswax, spermaceti, myristyl myristate, stearyl stearate.

14. Beeswax derivatives, e.g. polyoxyethylene sorbitol beeswax. These are reaction products of beeswax with ethoxylated sorbitol of varying ethylene oxide content, forming a mixture of ether esters.

15. Vegetable waxes including carnauba and candelilla waxes.

16. Phospholipids such as lectithin and derivatives.

17. Sterols. Cholesterol, cholesterol fatty acid esters are examples thereof.

18. Amides such as fatty acid amides, ethoxylated fatty acid amides, solid fatty acid alkanolamides.

Amounts of the above listed emollients may range anywhere from about 0.5 to about 40% by weight of the total composition. Preferably the amounts of these emollients will range from about 2 to about 25%, optimally between about 5 and 15% by weight.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by weight of the composition.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include dimethyl polysiloxane (CTFA name dimethicone), a polysiloxane end-blocked with trimethyl units and polydimethylcyclosiloxane, (CTFA name cyclomethicone). The preferred siloxanes exhibit a viscosity from about 2 to 50 centistokes at 25° C. Amounts of the silicones can range up to 30% by weight of the compositions, preferably from about 1 to about 10% by weight.

The emulsions of the invention can also include thickeners/viscosifiers in amounts up to about 5% by weight of the composition. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses, and cross-linked acrylic acid polymers such as those sold by B.F. Goodrich under the Carbopol trademark.

Preservatives can desirably be incorporated into the cosmetic compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choos them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Amounts of water in the composition may range anywhere from about 1 to about 99%, preferably from about 40 to about 90%, optimally between about 60 and 85% by weight.

Minor adjunct ingredients may also include fragrances, antifoam agents, bacteriostats, opacifiers and colorants, each in their effective amounts to accomplish their respective functions.

Th following examples will more fully illustrate the embodiments of this invention. All parts, percentages and proportions referred to herein and in the appended claims are by weight unless otherwise indicated.

EXAMPLE 1

An emulsion typical of the present invention is provided in Table I.

TABLE I

| Ingredients | Base Formula Weight % | |
|---|---|---|
| Cetyl Alcohol | 2.500 | |
| Glyceryl Monostearate | 1.500 | |
| Isopropyl Palmitate | 2.000 | Phase A |
| Petrolatum USP | 2.000 | |
| Propyl Paraben | 0.100 | |
| Deionized Water | 78.395 | |
| Glycerin USP | 10.000 | |
| Quatrisoft LM-200[1] | 0.250 | |
| Monaquat P-TS[2] | 3.000 | Phase B |
| Antifoam AF[3] | 0.005 | |
| Methyl Paraben | 0.150 | |
| Titanium Dioxide[4] | 0.100 | |
| | 100.000 | |

[1]Alkyl Substituted Water Soluble Cationic Polysaccharide, (Unio Carbide).
[2]Phosphate Tris Alkylamido Tri Quaternary Compound, (Mona Industries).
[3]Dimethicone Emulsion, (Dow Corning).
[4]Water Dispersable TiO$_2$, (Whittaker, Clark and Daniels)

The base formula outlined in Table I was prepared by first dispersing Quatrisoft LM-200 in glycerin. Thereafter, the Monaquat P-TS and water were combined into the glycerin dispersion. The resultant mixture was heated under moderate stirring at 70° C. Methyl paraben, titanium dioxide and antifoam AF were then added to the aqueous Phase B.

Separately prepared was an oil Phase A wherein cetyl alcohol, glyceryl monostearate, isopropyl palmitate, petrolatum USP and propyl paraben were combined under heating at 70° C. Phase A was then added to Phase B with moderate stirring. The combined phases were then homogenized until a white emulsion was achieved. This emulsion was then cooled to 32° C. with stirring.

EXAMPLE 2

Effects of various cationic polymers in the Base Formula were investigated for their freeze-thaw properties. These formulations were subjected to three freeze-thaw cycles from −18° to 22° C. and their appearances were recorded under Table II.

TABLE II

| | | Freeze-Thaw Cycles | | |
|---|---|---|---|---|
| No. | Polymer* | 1 | 2 | 3 |
| 1 | None | Grainy | Grainy | Grainy |
| 2 | Quatrisoft LM200 | Smooth | Smooth | Smooth |
| 3 | Polymer JR-400 | Grainy | Grainy | Grainy |
| 4 | Polymer JR-125 | Grainy | Grainy | Grainy |
| 5 | Polymer JR-30M | Grainy | Grainy | Grainy |
| 6 | Jaquar C-13S | Smooth | Smooth | Grainy |
| 7 | HyCare 1000 | Smooth | Grainy | Grainy |
| 8 | Celquat H-100 | Slightly Grainy | Slightly Grainy | Grainy |
| 9 | Celquat L-200 | Grainy | Grainy | Grainy |
| 10 | Crodacel AQ | Smooth | Smooth | Smooth |

*All polymers were incorporated at 0.25% weight active level.

From the results listed under Table II, it is seen that certain types of cationic polymers exhibit much better freeze-thaw stability. Particularly effective are Quatrisoft LM200 and Codacel AQ. On the other hand, cationic polymers such as the Polymer JR series exhibit graininess.

EXAMPLE 3

A series of different quaternary ammonium functionalized phosphate esters were evaluated with respect to freeze-thaw cycle properties. Each of the formulas incorporated 3% of the phosphate ester into the Base Formula shown in Example 1. Table III lists the results of the freeze-thaw cycle tests.

TABLE III

| | | Freeze-Thaw Cycles | | |
|---|---|---|---|---|
| No. | Phosphate Ester | 1 | 2 | 3 |
| 1 | Monaquat P-TS | Smooth | Smooth | Smooth |
| 2 | Monaquat P-TC | Smooth | Smooth | Smooth |
| 3 | Monaquat P-TD | Smooth | Smooth | Smooth |
| 4 | Monaquat P-TL | Grainy | Grainy | Grainy |
| 5 | Monaquat P-TZ | Grainy | Grainy | Grainy |
| 6 | Phospholipid EFA | Smooth | Smooth | Smooth |

Evident from Table III is that the Base Formula with either Monaquat P-TS, P-TC, or P-TD of Phospholipid EFA provides excellent freeze-thaw cycle properties. Relatively poor performance in terms of graininess was exhibited by Monaquat P-TL and P-TZ.

EXAMPLE 4

A series of commercial hand and body lotions were evaluated against formulations of the present invention utilizing the Porcine Skin Moisturization Assay. This test was used to detect differences in the moisture absorption/desorption and resistance to wash-off of lotions on porcine skin.

The test involved accurate weighing of 6 uniform pieces of porcine skin. These pieces were hydrated and then the test lotion applied. Periodically, the skin pieces were weighed at their reduced relative humidity. Directly after each weighing the pieces were uniformly rinsed in water and weighed once again under reduced relative humidity. Pre-rinse and post-rinse curves of weight versus time were graphed. Total areas under the dry-out curve before and after rinsing were then determined. Table IV lists results of these evaluations.

TABLE IV

| No. | TEST LOTION | TOTAL AREA PRE-RINSE | TOTAL AREA POST-RINSE |
|---|---|---|---|
| 1 | Eversoft ® | 1990.8 | −615.8 |
| 2 | Lubriderm ® | 2268.5 | 1154.4 |
| 3 | Keri Lotion ® | 1659.8 | −1008.5 |
| | Test Cationic Lotion 5% Glycerin | | |
| 4 | Monaquat P-TS/Quatrisoft LM-200 | 3535.8 | 1947.2 |
| | Test Cationic Lotion 10% Glycerin | | |
| 5 | Monaquat P-TS/Quatrisoft LM-200 | 4560.0 | 1965.7 |
| 6 | Monaquat P-TS/Crodacel QL | 3865.4 | 3337.4 |
| 7 | Monaquat P-TS/No Polymer | 3865.4 | 3512.2 |
| | Test Nonionic Lotion 10% Glycerin | | |
| 8 | No Monaquat/Quatrisoft LM-200 | 3391.3 | 587.18 |

Test lotions utilizing Monaquat P-TS exhibited post-rinse area results were superior to competitive products. Poor results were obtained when only Quatrisoft LM-200 was utilized in the absence of any Monaquat.

Although this invention has been described with reference to specific examples, it will be apparent to one skilled in the art that various modifications may be made thereto which fall within the scope and purview of the invention.

What is claimed is:

1. An aqueous composition comprising:
(i) from about 0.10 to about 30% of a quaternary ammonium functionalized phosphate ester having the formula:

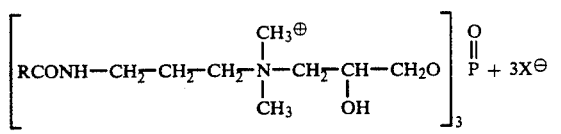

wherein R is an alkyl group having from 5 to 17 carbon atoms and X is an anion; and
(ii) from about 0.10 to about 10% of a cationic polysaccharide.

2. A composition according to claim 1 wherein said phosphate ester is present in an amount from about 1 to about 5% by weight of the composition.

3. A composition according to claim 1 wherein said cationic polysaccharide is present in amount from about 0.2 to about 1% by weight of the composition.

4. A composition according to claim 1 wherein the phosphate ester is present as the main emulsifier and surfactant of the composition.

5. A composition according to claim 1 wherein the cationic polysaccharide is substituted with a quaternary ammonium group having at least one substituent on the nitrogen being an alkyl group from 12 to 22 carbon atoms in length.

6. A composition according to claim 5 wherein the alkyl is selected from the group consisting of lauryl, coco and stearyl radicals.

* * * * *